United States Patent [19]

Ragavan et al.

[11] Patent Number: 5,993,856

[45] Date of Patent: Nov. 30, 1999

[54] PHARMACEUTICAL PREPARATIONS AND METHODS FOR THEIR ADMINISTRATION

[75] Inventors: Vanaja V. Ragavan, Wynnewood; Gerrianne M. DiPiano, Malvern, both of Pa.

[73] Assignee: FemmePharma, Wayne, Pa.

[21] Appl. No.: 08/971,346

[22] Filed: Nov. 17, 1997

Related U.S. Application Data

[60] Provisional application No. 60/036,727, Jan. 24, 1997, and provisional application No. 60/052,578, Jan. 15, 1997.

[51] Int. Cl.$^6$ ....................................................... A61K 9/14
[52] U.S. Cl. .......................... 424/489; 424/422; 424/430; 424/433
[58] Field of Search ................................... 424/489, 430, 424/433, 422

[56] References Cited

U.S. PATENT DOCUMENTS

| | | | |
|---|---|---|---|
| 3,921,636 | 11/1975 | Zaffaroni . | |
| 4,081,533 | 3/1978 | Cheesman | 424/177 |
| 4,107,288 | 8/1978 | Oppenheim et al. | 424/22 |
| 4,272,398 | 6/1981 | Jaffe | 252/316 |
| 4,286,587 | 9/1981 | Wong | 128/127 |
| 4,291,028 | 9/1981 | Vorys | 424/238 |
| 4,292,315 | 9/1981 | Vorys | 424/240 |
| 4,391,797 | 7/1983 | Folkman et al. | 424/19 |
| 4,525,340 | 6/1985 | Lange et al. | 424/16 |
| 4,591,496 | 5/1986 | Cohen et al. | 424/15 |
| 4,673,405 | 6/1987 | Guittard et al. | 604/890 |
| 4,762,717 | 8/1988 | Crowley, Jr. et al. | 424/425 |
| 4,861,627 | 8/1989 | Mathiowitz et al. | 427/213.31 |
| 4,873,092 | 10/1989 | Azuma et al. | 424/499 |
| 4,965,128 | 10/1990 | Greidanus et al. | 424/423 |
| 4,997,653 | 3/1991 | Igarishi . | |
| 5,057,317 | 10/1991 | Iida | 424/423 |
| 5,091,185 | 2/1992 | Castillo et al. | 424/438 |
| 5,130,137 | 7/1992 | Crowley, Jr. | 424/422 |
| 5,145,684 | 9/1992 | Liversidge et al | 424/489 |
| 5,156,851 | 10/1992 | Castillo et al. | 424/497 |
| 5,324,522 | 6/1994 | Krenning et al. | 424/456 |
| 5,330,768 | 7/1994 | Park et al. | 424/501 |
| 5,340,585 | 8/1994 | Pike et al. | 424/426 |
| 5,359,030 | 10/1994 | Ekwuribe | 530/303 |
| 5,413,797 | 5/1995 | Khan et al. | 424/489 |
| 5,417,982 | 5/1995 | Modi | 424/489 |
| 5,438,040 | 8/1995 | Ekwuribe | 514/3 |
| 5,472,704 | 12/1995 | Santus et al. | 424/435 |
| 5,482,927 | 1/1996 | Maniar et al. | 514/12 |
| 5,494,047 | 2/1996 | Van Os | 424/563 |
| 5,510,118 | 4/1996 | Bosch et al. . | |
| 5,633,011 | 5/1997 | Dong et al. | 424/489 |
| 5,643,604 | 7/1997 | Angeles Uribe et al. | 424/489 |
| 5,651,976 | 7/1997 | Price et al. | 424/409 |
| 5,665,383 | 9/1997 | Grinstaff et al. | 424/450 |

FOREIGN PATENT DOCUMENTS

| | | |
|---|---|---|
| 0 501 056 | 9/1992 | European Pat. Off. . |
| 0 566 135 | 10/1993 | European Pat. Off. . |
| WO 95/07071 | 3/1995 | WIPO . |
| WO 96/37232 | 11/1996 | WIPO . |

OTHER PUBLICATIONS

Mathiowitz, et al., "Morphology of Polyanhydride Microsphere Delivery System," *Scanning Microscopy* 4(2):329–340 (1990).

Mathiowitz, et al., "Polyanhydride Microspheres. IV. morphology and Characterization of Systems Made by Spray Drying," *J. Appl. Polymer Sci.* 45:125–134 (1992).

Mizutani, et al., "Danazol concentrations in ovary, uterus, and seum and their effect on the hypothalamic–pituitary–ovarian axis during vaginal administration of a danazol suppository," *Fertility and Sterility* 63(6):1184–1189 (1995).

Salib, et al., "Utilization of Sodium Alginate in Drug Microencapsulation," *Pharmazeutische Industie* 40–11A:1230–1234 (1978).

"The First Uterine Pass Effect—A new finding for new options in progresterone therapy," (West–Ayerst International, Inc., 1995).

Benita, et al., "Characterization of Drug–Loaded Poly(d, N–lactide) Microspheres" *J. Pharm. Sci.* 73(12):1721–1724 (1984).

Braun, et al., "Effect of danazol in vitro and in vivo on monocyte–mediated enhancement of endometrial cell proliferation in women with endometriosis," *Fertility and Sterility* 62(1):89–95 (1994).

De Ziegler, et al., "Administration Non–Orale De La Progestérone: Expériences et Avenir De La Voie Transvaginale," *Rev. Med. Suisse Romande*, pp. 13–28 (1994).

Farquhar, "Management of Dysfunctional Uterine Bleeding," *Drugs* 44(4):378–384 (1992).

(List continued on next page.)

*Primary Examiner*—Terressa Mosley
*Attorney, Agent, or Firm*—Arnall Golden & Gregory, LLP

[57] ABSTRACT

Formulations which have been developed for topical or local delivery intrapelvically, intraperitoneally or directly on reproductive organs of interest administration to a region such as the female reproductive system, provide for increased comfort, increased bioavailability, rapid and relatively high blood levels in the regions to be treated in the substantial absence of systemic levels of drug which might cause side effects. These formulations consist of drug micro or nanoparticles, which may be formed of drug alone or in combination with an excipient or polymeric carrier. The excipient or polymer may be used to manipulate release rates and to increase adhesion to the affected region. The particulate formulation can be applied as a dried powder, a liquid suspension or dispersion, or as a topical ointment, creme, lotion, foam or suppository.

33 Claims, No Drawings

OTHER PUBLICATIONS

Hull, et al., "Endometriosis: An Enigmatic Disease," *Journal of Women's Health* 5(2):111–120 (1996).

Igarishi, "A New Therapy for Pelvic Endometriosis and Uterine Adenomyosis: Local Effect of Vaginal and Intrauterine Danazol Application," *Asia–Oceania J. Obstet. Gynaecol.* 16(1):1–12 (1990).

Lim, et al., "Micoencapsulation of Living Cells and Tissues," *J. Pharm. Sci.* 70(4):351–354 (1981).

Lobo, "Vaginal Route Paradox: A Direct Transport to the Uterus," *Symposium: The First Uterine Pass Effect*, (Wyeth–Ayerst International, Inc., 1995).

Mathiowitz, et al., "Novel Microcapsules for Delivery Systems," *Reactive Polyymers* 6:275–283 (1987).

Mathiowitz, et al., "Polyanhydride Microspheres as Drug Carriers I. Hot–Melt Microencapsulation," *J. Controlled Release* 5:13–22.

Mathiowitz, et al., "Polyanhydride Microspheres as Drug Carriers. II. Microencapsulation by Solvent Removal," *J. Appl. Polymer Sci.* 35:755–774 (1988).

PHARMACEUTICAL PREPARATIONS AND METHODS FOR THEIR ADMINISTRATION

This application claims priority to U.S. Ser. No. 60/036,727, filed Jan. 24, 1997 expired entitled "Microparticle Enhanced Delivery of Pharmaceuticals" and U.S. Ser. No. 60/052,578, filed Jul. 15, 1997 expired entitled "Non-Oral Delivery of Pharmaceuticals in the Treatment of Endometriosis", both by Vanaja V. Ragavan and Geriannn M. Dipiano.

FIELD OF THE INVENTION

The present invention relates to pharmaceutical preparations, and especially pharmaceutical formulations that can be introduced topically, locally, intrapelvic, intraperitoneal or directly on reproductive organs of interest in amounts effective to treat various conditions, particularly local diseases of female reproductive system, such as pelvic, uterine, cervical and vaginal diseases which are present in this region of the body.

BACKGROUND OF THE INVENTION

It has long been known that treatment of female reproductive diseases by traditional methods of oral or systemic administration is associated with drug bioavailability problems and concomitant side effect complications from unwanted absorption of drugs into the systemic circulation. For example, normal digestive tract action may break down orally administered active ingredients to decrease effective drug delivery dosages, or the pharmaceutical preparation is changed by passage through the liver or by systemic circulation or may not achieve adequate levels in the area of interest. To counteract these undesirable actions, the dosage of the active ingredient needs to be increased, oftentimes leading to undesirable side effects.

In the case of danazol, an isoxazolo derivative of 17 ethenyltestosterone (an androgen hormone) which is commonly administered to women for treatment of endometriosis in dosages of up to 800 mg daily, and at such higher doses, adverse side effects are seen which may include weight gain, voice change, development of facial and chest hair, loss of libido, acne, and central nervous system ("CNS") symptoms such as depression, anxiety, fatigue, nausea and diarrhea, as well as the inhibition of pregnancy while undergoing treatment. See, for example, Spooner, *Classification of Side Effects to Danazol Therapy*, Winthrop Laboratories, Surrey, England.

It is therefore highly desirable to provide new systems and methods for the administration of pharmaceuticals which would avoid such drawbacks. Mizutani, et al., in *Fertility and Sterility* 63, 1184–1189 (1995), describes administration of danazole vaginally by means of a 100 mg suppository, and compared the results with oral administration of a 400 mg dosage. No effect on the hypothalamic-pituitary-ovarian axis was noted, although high concentrations were present in the ovary, uterus and serum, with insignificant serum levels, following vaginal administration. Mizutani, et al., conducted their study following a report by Igarishi, *Asia-Oceania J. Obstet. Gynaecol.* 16(1), 1–12 (1990), that administration vaginally of danazole in a silicone vaginal ring reduced endometriotic tissue in the uterus and increased the incidence of pregnancy in treated women to a statistically significant degree. The immediate drawback to both therapies, however, is the formulation and delivery platform such as vaginal rings and other devices are particularly unsatisfactory for women who already suffer from the cramps and pains associated with endometriosis. The dosages which were used were also quite high and extremely variable and may potentially have a negative and accumulative depot effect.

It is therefore an object of the present invention to provide formulations which are effective in treating disorders of the reproductive organs which has high patient compliance and comfort.

It is a further object of the present invention to provide formulations and methods of administration which provide for extremely rapid uptake of drug in the affected region, with low systemic concentrations and few concordant side effects.

It is still another object of the present invention to provide greatly enhanced bioavailability of drug in formulations administered topically or locally, intrapelvically, intraperitoneally or directly on reproductive organs of interest as compared to the drugs administered in controlled release devices.

SUMMARY OF THE INVENTION

Formulations which have been developed for topical or local delivery intrapelvically, intraperitoneally or directly on reproductive organs of interest administration to a region such as the female reproductive system, provide for increased comfort, increased bioavailability, rapid and relatively high blood levels in the regions to be treated in the substantial absence of systemic levels of drug which might cause side effects. These formulations consist of drug micro or nanoparticles, which may be formed of drug alone or in combination with an excipient or polymeric carrier. The excipient or polymer may be used to manipulate release rates and to increase adhesion to the affected region. The particulate formulation can be applied as a dried powder, a liquid suspension or dispersion, or as a topical ointment, creme, lotion, foam or suppository.

Rat studies demonstrate rapid uptake of danazole into the tissues affected in endometriosis, with serum drug levels that are almost undetectable.

DETAILED DESCRIPTION OF THE INVENTION

The compositions and methods for administration thereof provide for significantly diminished side effects with increased bioavailability and comfort, as compared to conventional drug administration techniques, avoiding oral and parenteral administration, the use of complex and expensive biocompatible polymeric material, and the elimination of the need for insertion and maintenance of potentially infectious foreign objects into the body such as intrauterine devices, vaginal rings, and suppositories.

I. Formulations.

The formulations are designed to provide maximum uptake in the affected tissues with rapid dissemination throughout the region to be treated, with little to no increase in systemic blood levels of the drug. The formulations can consist solely of drug, or drug combined with excipient or polymeric material.

A. Drugs

The term "drug" can refer to any pharmaceutically active substance capable of being administered in a particulate formulation, which achieves the desired effect. Drugs can be synthetic or isolated natural organic compounds, proteins or peptides, oligonucleotides or nucleotides, or polysaccharides or sugars. Drugs may have any of a variety of activities, which may be inhibitory or stimulatory, such as antibiotic activity, antiviral activity, antifungal activity, steroidal activity, cytotoxic or anti-proliferative activity, anti-inflammatory activity, analgesic or anesthetic activity, as well as contrast or other diagnostic agents. A description of these classes of drugs and listing of species within each class can be found in Martindale, *The Extra Pharmacopoeia*, 31st Ed., *The Pharmaceutical Press*, London (1996) and goodman and Gilman, *The Pharmacological Basis of Therapeutics*, (th Ed., McGraw-Hill Publishing company (1996).

In a preferred embodiment, the drug is danazole is a micro or nanoparticulate formulation. This can be achieved by milling of the drug or atomization of drug solution, for example, into a solvent extraction fluid, or other standard techniques.

B. Excipients or Carriers

The drug substance may be "associated" in any physical form with a particulate material, for example, adsorbed or absorbed, adhered to or dispersed or suspended in such matter, which may take the form of discrete particles or microparticles in any medicinal preparation, and/or suspended or dissolved in a carrier such as an ointment, gel, paste, lotion, or spray.

Standard excipients include gelatin, casein, lecithin, gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidol silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethycellulose phthalate, noncrystalline cellulose, magnesium aluminum silicate, triethanolamine, polyvinyl alcohol, polyvinylpyrrolidone, sugars and starches.

In a preferred embodiment, the drug is present on or within micro or nanoparticulates formed of a polymeric material. Polymers can be used to increase adhesion to mucosal surfaces, to control release as a function of the diffusion rate of drugs out of the polymeric matrix and/or rate of degradation by hydrolysis or enzyme degradation of the polymers and/or pH alteration, and to increase surface area of the drug relative to the size of the particle. Additional materials, such as diagnostic agents, including echogenic gases, radioactive materials—which may also in themselves be therapeutic, and magnetic materials for detection by MRI or PET, can be included in the drug and/or polymer.

1. Polymeric Materials

Generally, two classes of polymers have appeared to show useful bioadhesive properties: hydrophilic polymers and hydrogels. In the large class of hydrophilic polymers, those containing carboxylic groups (e.g., poly[acrylic acid]) exhibit the best bioadhesive properties. One could infer that polymers with the highest concentrations of carboxylic groups should be the materials of choice for bioadhesion on soft tissues. In other studies, the most promising polymers were sodium alginate, carboxymethylcellulose, hydroxymethylcellulose and methylcellulose. Some of these materials are water-soluble, while others are hydrogels.

Rapidly bioerodible polymers such as poly[lactide-co-glycolide], polyanhydrides, and polyorthoesters, whose carboxylic groups are exposed on the external surface as their smooth surface erodes, are excellent candidates for bioadhesive drug delivery systems. In addition, polymers containing labile bonds, such as polyanhydrides and polyesters, are well known for their hydrolytic reactivity. Their hydrolytic degradation rates can generally be altered by simple changes in the polymer backbone.

Representative natural polymers include proteins, such as zein, modified zein, casein, gelatin, gluten, serum albumin, or collagen, and polysaccharides, such as cellulose, dextrans, polyhyaluronic acid, polymers of acrylic and methacrylic esters and alginic acid. Representative synthetic polymers include polyphosphazines, poly(vinyl alcohols), polyamides, polycarbonates, polyalkylenes, polyacrylamides, polyalkylene glycols, polyalkylene oxides, polyalkylene terephthalates, polyvinyl ethers, polyvinyl esters, polyvinyl halides, polyvinylpyrrolidone, polyglycolides, polysiloxanes, polyurethanes and copolymers thereof. Synthetically modified natural polymers include alkyl celluloses, hydroxyalkyl celluloses, cellulose ethers, cellulose esters, and nitrocelluloses. Other polymers of interest include, but are not limited to, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, cellulose sulfate sodium salt, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate) polyethylene, polypropylene, poly (ethylene glycol), poly(ethylene oxide), poly (ethylene terephthalate), poly(vinyl acetate), polyvinyl chloride, polystyrene, polyvinyl pyrrolidone, and polyvinylphenol. Representative bioerodible polymers include polylactides, polyglycolides and copolymers thereof, poly(ethylene terephthalate), poly(butic acid), poly(valeric acid), poly (lactide-co-caprolactone), poly[lactide-co-glycolide], polyanhydrides, polyorthoesters, blends and copolymers thereof.

Examples of biodegradable polymers include synthetic polymers such as polymers of lactic acid and glycolic acid, polyanhydrides, poly(ortho)esters, polyurethanes, poly (butic acid), poly(valeric acid), and poly(lactide-co-caprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

These polymers can be obtained from sources such as Sigma Chemical Co., St. Louis, Mo., Polysciences, Warrenton, Pa., Aldrich, Milwaukee, Wis., Fluka, Ronkonkoma, N.Y., and BioRad, Richmond, Calif. or else synthesized from monomers obtained from these suppliers using standard techniques. Both non-biodegradable and biodegradable matrices can be used for delivery of drugs, although biodegradable matrices are preferred. These may be natural or synthetic polymers, although synthetic polymers are preferred due to the better characterization of degradation and release profiles. The polymer is selected based on the period over which release is desired, generally in the range of at least immediate release to release over a period of twelve months, although longer periods may be desirable. In some cases linear release may be most useful, although in others a pulse release or "bulk release" may provide more effective results. The polymer may be in the form of a hydrogel (typically absorbing up to about 90% by weight of water), and can optionally be crosslinked with multivalent ions or polymers.

High molecular weight drugs can be delivered partially by diffusion but mainly by degradation of the polymeric system. In this case, biodegradable polymers, bioerodible hydrogels, and protein delivery systems are particularly preferred.

Examples of non-biodegradable polymers include ethylene vinyl acetate, poly(meth)acrylic acid, polyamides, copolymers and mixtures thereof.

2. Methods of Making Particles

In the preferred embodiment, the polymeric matrix is between nanometers and one millimeter in diameter, more preferably between 0.5 and 100 microns. The microparticles can be drug/polymer particles, microspheres, where drug is dispersed within a solid polymeric matrix, or microcapsules, where the core is of a different material than the polymeric shell, and the drug is dispersed or suspended in the core, which may be liquid or solid in nature. Unless specifically defined herein, microparticles, microspheres, and microcapsules are used interchangeably.

The matrices can be formed by solvent evaporation, spray drying, solvent extraction and other methods known to those skilled in the art, for example, as described by Mathiowitz and Langer, *J. Controlled Release* 5, 13–22 (1987); Mathiowitz, et al., *Reactive Polymers* 6, 275–283 (1987); and Mathiowitz, et al., *J. Appl. Polymer Sci.* 35, 755–774 (1988), the teachings of which are incorporated herein. The selection of the method depends on the polymer selection, the size, external morphology, and crystallinity that is desired, as described, for example, by Mathiowitz, et al., *Scanning Microscopy* 4, 329–340 (1990); Mathiowitz, et al., *J. Appl. Polymer Sci.* 45, 125–134 (1992); and Benita, et al., *J. Pharm. Sci.* 73, 1721–1724 (1984), the teachings of which are incorporated herein.

In solvent evaporation, described for example, in Mathiowitz, et al., (1990), Benita, and U.S. Pat. No. 4,272,398 to Jaffe, the polymer is dissolved in a volatile organic solvent. The drug, either in soluble form or dispersed as fine particles, is added to the polymer solution, and the mixture is suspended in an aqueous phase that contains a surface active agent such as poly(vinyl alcohol). The resulting emulsion is stirred until most of the organic solvent evaporates, leaving solid microspheres.

In general, the polymer can be dissolved in methylene chloride. Several different polymer concentrations can be used, for example, between 0.05 and 0.20 g/ml. After loading the solution with drug, the solution is suspended in 200 ml of vigorously stirring distilled water containing 1% (w/v) poly(vinyl alcohol) (Sigma Chemical Co., St. Louis, Mo.). After four hours of stirring, the organic solvent will have evaporated from the polymer, and the resulting microspheres will be washed with water and dried overnight in a lyophilizer.

Microspheres with different sizes (between 1 nanometer and 1000 microns) and morphologies can be obtained by this method which is useful for relatively stable polymers such as polyesters and polystyrene. However, labile polymers such as polyanhydrides may degrade due to exposure to water. For these polymers, hot melt encapsulation and solvent removal may be preferred.

In hot melt encapsulation, the polymer is first melted and then mixed with the solid particles of drug, preferably sieved to less than 50 $\mu$m. The mixture is suspended in a non-miscible solvent such as silicon oil and, with continuous stirring, heated to 5° C. above the melting point of the polymer. Once the emulsion is stabilized, it is cooled until the polymer particles solidify. The resulting microspheres are washed by decantation with petroleum ether to give a free-flowing powder. Microspheres with diameters between one and 1000 microns can be obtained with this method. The external surface of spheres prepared with this technique are usually smooth and dense. This procedure is useful with water labile polymers, but is limited to use with polymers with molecular weights between 1000 and 50000.

Solvent removal was primarily designed for use with polyanhydrides. In this method, the drug is dispersed or dissolved in a solution of a selected polymer in a volatile organic solvent like methylene chloride. The mixture is then suspended in oil, such as silicon oil, by stirring, to form an emulsion. Within 24 hours, the solvent diffuses into the oil phase and the emulsion droplets harden into solid polymer microspheres. Unlike solvent evaporation, this method can be used to make microspheres from polymers with high melting points and a wide range of molecular weights. Microspheres having a diameter between one and 300 microns can be obtained with this procedure. The external morphology of the spheres is highly dependent on the type of polymer used.

In spray drying, the polymer is dissolved in methylene chloride (0.04 g/ml). A known amount of active drug is suspended (if insoluble) or co-dissolved (if soluble) in the polymer solution. The solution or the dispersion is then spray-dried. Typical process parameters for a mini-spray drier are as follows: polymer concentration=0.04 g/ml, inlet temperature=24° C., outlet temperature=13 to 15° C., aspirator setting=15, pump setting=10 ml/min, spray flow=600 NLh$^{-1}$, and nozzle diameter=0.5 mm. Microspheres ranging in diameter between one and ten microns can be obtained with a morphology which depends on the selection of polymer.

Double walled microspheres can be prepared according to U.S. Pat. No. 4,861,627 to Mathiowitz.

Hydrogel microspheres made of gel-type polymers such as alginate or polyphosphazenes or other dicarboxylic polymers can be prepared by dissolving the polymer in an aqueous solution, suspending the material to be incorporated into the mixture, and extruding the polymer mixture through a microdroplet forming device, equipped with a nitrogen gas jet. The resulting microspheres fall into a slowly stirring, ionic hardening bath, as described, for example, by Salib, et al., *Pharmazeutische Industrie* 40–11A, 1230 (1978), the teachings of which are incorporated herein. The advantage of this system is the ability to further modify the surface of the microspheres by coating them with polycationic polymers such as polylysine, after fabrication, for example, as described by Lim, et al., *J. Pharm. Sci.* 70, 351–354 (1981). For example, in the case of alginate, a hydrogel can be formed by ionically crosslinking the alginate with calcium ions, then crosslinking the outer surface of the microparticle with a polycation such as polylysine, after fabrication. The microsphere particle size will be controlled using various size extruders, polymer flow rates and gas flow rates.

3. Exemplary Formulations

Many specific drug formulations have been described in the literature. For example, U.S. Pat. No. 5,145,684 describes dispersible particles consisting of a drug substance having a surface modifier adsorbed on its surface to maintain an effective average particle size of less than about 400 nanometers. U.S. Pat. No. 5,472,704 describes pharmaceutical compositions for the controlled release of various drugs said to have the properties of adhering to biologic tissues. These compositions are clusters of pharmaceutically active ingredients, each of which are substantially and completely coated with an adhesive polymeric coating substance, in which the coating also comprises a physiologically acceptable adhesive polymer in amounts efficient to adhere to a mucous membrane. These compositions can be adapted for oral, ocular, rectal, vaginal, nasal, and periodontal administration. U.S. Pat. No. 5,340,585 discusses compositions and methods to treat gynecological disorders for extended periods. U.S. Pat. No. 4,107,288 discusses particles in a size range from about 10 to about 1000 nanometers formed of a cross-linked matrix of macromolecules which can include gum, soluble cellulose, or proteins such as gelatin or albumin, and which a biologically or pharmacodynamically active material is supported on or incorporated into these cross-linked matrices. As the active substance is enclosed and adsorbed into the structure of the particles, selective long-term therapy can be carried out in which the organism is subjected to only a minimum of biologically or pharmacodynamically active substance. U.S. Pat. No. 4,997,653 describes a preparation containing danazol in a matrix base of a topical drug delivery system. These topical matrix-based preparations are said to be of any shape commonly employed for insertion into the uterus or vagina.

II. Methods of Administration

The formulations are preferably administered locally within the region to be treated, for example, vaginally for treatment of diseases of the ovaries and uterus. As used herein, "locally" can refer to topical application generally to the mucosal or endometrial surfaces of the vagina and/or uterus, or to a particular portion of the vagina or uterus. As used herein, "regionally" refers to reproductive organs and their surrounding environs, which include uterus, fallopian tube, peritoneal space, pelvic cul-de-sac, ovaries, perineum, and the rectovaginal region. As used herein, "systemically" refers to the circulatory system, and regions outside the spaces described above.

Vaginally administered pharmaceutical preparations as described herein are particularly effective in treating certain diseases of female reproductive systems, such as the administration of danazol for treatment of endometriosis. It is desirable to administer the danazol formulations locally with dosages which are less than other modes of delivery, such as oral delivery. Transdermal doses are usually found to be one-quarter of the oral dose for similar efficacy. In this instance, it is possible to lower the dose even lower (the ring delivered between about 1 and 2 mg/day). Such dosage administration will ensure negligible or relatively low serum levels of danazol to avoid undesirable side effects associated with oral dosing, such as hirsutism and other androgenic side effects.

The following non-limiting examples more fully demonstrate the present invention.

EXAMPLE 1
Preparation of Gel Products

The drug substance, micronized danazol (carrying DMF-Drug Master File Certification) was manufactured by Cipla Pharmaceuticals and bought from Byron Chemical Company. UV absorption identified the drug substance as being identical to Danazol USP. Individual impurity was noted to be more than 0.5%, and total impurities not more than 1.0%. Assay of dried basis was between 97% and 102% w/w on dried basis. More than 90% of the particles were less than 5 microns in diameter and the remaining particles were between 5 and 15 microns in diameter.

Micronized danazol was levigated in a commercial preparation of KY Jelly, which is made up of a polymer hydroxyethyl cellulose to 10 ml volume (based on weight using density of jelly of 2.16 g/ml) for 1 mg per 50 $\mu$l concentration. Gels were smooth in consistency, uniformly white and flowable. Particle size measurements were conducted with a Coulter H4mD particle size analyser and were noted to be as follows:

Danazol Powder:

| Average of 6 measurements | 3.2 $\mu$ |
|---|---|
| Individual measurement and variation | 3.2 $\mu$ ± 9 $\mu$ |

1 mg gel:

| Average of 5 measurements | 3.0 $\mu$ |
|---|---|
| Individual measurement and variation | 3.4 $\mu$ ± 1.5 $\mu$ |

EXAMPLE 2
Administration of Danazole Microparticulate Formulation to Rats.

Mature female Sprague-Dawley rats were used for the experiment. 1 mg of the microparticulate danazol was delivered in a volume of 50 $\mu$l to the vaginal vault and the animals sacrificed at the times noted below. The uterus and ovaries were separately homogenized and blood was drawn. All tissues and biological samples were processed. Danazol was extracted and assayed by HPLC methodology.

Danazol Clinical Assay:

Danazol was extracted from serum and tissue hexane/chloroform 80/20. For tissues, 1 ml aliquote of each homogenate was taken. The extracted danazol was reconstituted in a water/acetonitrile mobile phase and a Beckman Ultrasphere 5 micron, 4.6 mm×15 cm reverse phase column (C-18 RP) was used for all the HPLC analyses. A danazol recovery study was conducted using danazol drug product. The recovery was determined by comparing the extracted signal with unextracted signal. A recovery of between 75 and 84% was obtained for the extraction method.

Study Results:

Tissue and serum levels are summarized below in Table 1:

TABLE 1

| Tissue and Serum Levels of Danazole in Rats | | | |
|---|---|---|---|
| RATE AND TIME | UTERUS-ng/g | OVARIES ng/g | SERUM ng/ml |
| 2 hours | 0.43 | 0.33 | 0.21 |
| 4 hours | 0.57 | not detected | not detected |
| 6 hours | 0.77 | not detected | not detected |

The results of this study demonstrate that the formulation used resulted in a preferential absorption of danazol into the uterus.

In the above examples, danazol concentrations of 1 mg/300 g rat were administered. In work by Mizutami, danazol concentrations of 100 mg/50 kg women were administered. These concentrations are roughly equivalent. The data demonstrate that the suppository used by Mizutami resulted in uterine concentrations of danazol which were $10^5$ times higher than the uterine concentrations of danazol provided by the microparticles in the above examples. Such high local concentrations could result in significant changes in the local delivery of the drug and effects on the reproductive organs, for instance, changes in hormone steroid responsiveness and depot effect.

Igarashi administered a vaginal ring contained in silicone. This type of drug delivery device releases drug in a constant manner, creating a continuous flow of drug and potentially to a depot effect. Igarashi discloses two examples in which danazol was administered via the vaginal ring. In both examples, the uterine concentration of danazol was 100 times higher than the uterine concentration in the above examples.

EXAMPLE 3

Protocol for Studies in Primate Models of Endometriosis.

Microparticle formulation allows for considerable decrease in delivered dose, increased bioavailability to the organs of interest with lower tissue concentrations.

Monkey Protocol:

The monkey study will demonstrate efficacy of the microparticle formulation in an animal model of endometriosis, while also evaluating systemic levels of locally delivered danazol. The simian model of endometriosis will be used to demonstrate efficacy and safety. The rationale for using monkeys is the finding that certain monkeys will naturally develop endometriosis which resembles, in crucial ways, the human disease. In addition, monkeys are a good model for studying the human female reproductive system, both anatomically and physiologically for testing a vaginal product such as Danazol TVDT. This study will assist in identifying the dose needed to treat human endometriosis and furthermore, corroborate preliminary evidence that danazol can be delivered vaginally for treatment of endometriosis with reduced systemic levels. Microparticle danazol will be formulated in the presence of poly(vinylpyrrilodine). Three doses of Danazol TVDT will be studied in monkeys with endometriosis and compared to orally delivered danazol as described below. The study will be a nine week, parallel, randomized study comparing the effects of oral danazol given at 200 mg daily and three doses of Danazol TVDT: at 10 mg/day; (one-twentieth the oral dose), 25 mg/day (one-tenth the oral dose) and 50 mg/day, (one quarter the oral dose). The results will demonstrate local delivery of microparticle danazol results in efficacy and low systemic levels.

Modifications and variations of the present invention will be obvious to those skilled in the art from the foregoing description. These modifications and variations are intended to come within the scope of the appended claims.

We claim:

1. A micro or nanoparticulate drug formulation for local or regional topical administration of an effective amount to provide relief from symptoms associated with a disease or disorder in a region in patients in need thereof, wherein the effective amount is less than the effective amount when the drug is administered systemically.

2. The formulation of claim 1 wherein the region is the female reproductive organs.

3. The formulation of claim 2 wherein the patients have a disorder located in the reproductive organs.

4. The formulation of claim 1 wherein the formulation comprises drug particles.

5. The formulation of claim 3 wherein the drug is for treatment of endometriosis.

6. The formulation of claim 1 wherein the micro or nano particulates adhere to mucosal tissue.

7. The formulation of claim 1 where the micro or nano particulates comprise polymer altering rates of drug absorption in the region to be treated.

8. The formulation of claim 1 which can be administered vaginally, intraperitoneally, or directly on the reproductive organs of interest.

9. The formulation of claim 8 wherein the drug is danazol and wherein the formulation is suitable for vaginal administration in patients in need thereof and is in a dosage effective for treatment of endometriosis.

10. The formulation of claim 1 wherein the drug is an anticancer drug, cytotherapeutic or anti-proliferative drug in a dosage effective for treatment of cancer in the region of the patient where administered.

11. The formulation of claim 1 wherein the drug is an antiviral agent effective for treatment of viral infections selected from genital herpes and genital papilloma viral infections.

12. The formulation of claim 1 wherein the drug is an antifungal agent effective for treatment of vaginal fungal infections.

13. The formulation of claim 1 wherein the drug is an antibacterial agent effective for treatment of vaginal and endometrial bacterial infections.

14. The formulation of claim 1 wherein the drug is a steroid or steroid-like product suitable for treatment of endocrine conditions.

15. The formulation of claim 14 wherein the drug is effective for treatment of menopause, infertility, contraception, dysfunctional uterine bleeding, dysmenorrhea, adenomyosis, or assisted reproductive technologies.

16. A method of treating a patient comprising the step of topically administering to the patient an effective amount of a micro or nanoparticulate drug formulation suitable for local or regional topical administration of an effective amount to provide relief from symptoms associated with a disease or disorder in a region in the patient in need thereof, wherein the effective amount is less than the effective amount when the drug is administered systemically.

17. The method of claim 16 wherein the region is the female reproductive organs.

18. The method of claim 16 wherein the patients have a disorder located in the reproductive organs.

19. The method of claim 18 wherein the drug is for treatment of endometriosis and the patient has endometriosis.

20. The method of claim 17 which can be administered vaginally, intraperitoneally, or directly on the reproductive organs of interest.

21. The method of claim 16 wherein the drug is danazol and wherein the formulation is vaginally administered in patients in need thereof in a dosage effective for treatment of endometriosis.

22. The method of claim 16 wherein the drug is an anticancer drug, cytotherapeutic or anti-proliferative drug in a dosage effective for treatment of cancer in the region of the patient where administered.

23. The method of claim 16 wherein the drug is an antiviral agent effective for treatment of viral infections selected from genital herpes and genital papilloma viral infections.

24. The method of claim 16 wherein the drug is an antifungal agent effective for treatment of vaginal fungal infections.

25. The method of claim 16 wherein the drug is an antibacterial agent effective for treatment of vaginal and endometrial bacterial infections.

26. The method of claim 16 wherein the drug is a steroid or steroid-like product suitable for treatment of endocrine conditions.

27. The method of claim 26 wherein the drug is effective for treatment of menopause, infertility, contraception, dysfunctional uterine bleeding, dysmenorrhea, adenomyosis, or assisted reproductive technologies.

28. A method for treating endometriosis by decreasing the discomfort associated with endometriosis comprising administering to the mucosal membranes of the female reproductive tract danazole in a form promoting quick uptake into the blood stream, wherein the danazole is administered in an effective amount which is less than the effective amount when the drug is administered systemically.

29. The method of claim 28 wherein the danazole is in a form selected from the group consisting of foams, tablets, and creams.

30. The method of claim 28 wherein the danazole is in a form suitable for application to the uterus.

31. A composition for treating endometriosis comprising danazole in a form promoting quick uptake into the blood stream when applied to the mucosal membranes of the female reproductive tract, wherein danazole is in a form delivering an effective amount to decrease the discomfort of endometriosis which is less than the effective amount when the drug is administered systemically.

32. The composition of claim 31 wherein the danazole is in a form selected from the group consisting of foams, tablets, and creams.

33. The composition of claim 32 wherein the danazole is in a form suitable for application to the uterus.

* * * * *